(12) United States Patent
Butterfield et al.

(10) Patent No.: US 8,359,338 B2
(45) Date of Patent: Jan. 22, 2013

(54) SYSTEM AND METHOD FOR MANAGING MEDICAL DATABASES FOR PATIENT CARE DEVICES

(75) Inventors: Robert D. Butterfield, Poway, CA (US); Kathleen M. Jordan, San Diego, CA (US)

(73) Assignee: CareFusion 303, Inc., San Diego, CA (US)

( * ) Notice: Subject to any disclaimer, the term of this patent is extended or adjusted under 35 U.S.C. 154(b) by 1346 days.

(21) Appl. No.: 10/902,989

(22) Filed: Jul. 30, 2004

(65) Prior Publication Data

US 2006/0026205 A1 Feb. 2, 2006

(51) Int. Cl.
*G06F 17/30* (2006.01)
*G06F 7/00* (2006.01)

(52) U.S. Cl. .................................. 707/803; 707/965
(58) Field of Classification Search ............... 707/104.1, 707/965; 705/3
See application file for complete search history.

(56) References Cited

U.S. PATENT DOCUMENTS

| 5,041,086 A | | 8/1991 | Koenig et al. |
| 5,256,157 A | | 10/1993 | Samiotes et al. |
| 5,681,285 A | * | 10/1997 | Ford et al. ..................... 604/151 |
| 5,690,690 A | | 11/1997 | Nappholz et al. |
| 5,713,856 A | | 2/1998 | Eggers et al. |
| 5,772,635 A | | 6/1998 | Dastur et al. |
| 5,814,015 A | | 9/1998 | Gargano et al. |
| 5,819,229 A | * | 10/1998 | Boppe ............................. 705/2 |
| 5,861,017 A | * | 1/1999 | Smith et al. ..................... 607/59 |
| 5,873,731 A | * | 2/1999 | Prendergast ................. 434/262 |
| 5,935,099 A | * | 8/1999 | Peterson et al. ............... 604/65 |
| 5,983,140 A | * | 11/1999 | Smith et al. ..................... 607/59 |
| 6,012,034 A | * | 1/2000 | Hamparian et al. ............. 705/2 |
| 6,092,722 A | * | 7/2000 | Heinrichs et al. ............. 235/375 |
| 6,188,407 B1 | * | 2/2001 | Smith et al. ..................... 715/841 |
| 6,269,340 B1 | * | 7/2001 | Ford et al. ......................... 705/3 |
| 6,321,117 B1 | * | 11/2001 | Koshiol et al. ................. 607/59 |
| 2002/0120178 A1 | * | 8/2002 | Tartaglia et al. ............. 600/114 |
| 2002/0120187 A1 | | 8/2002 | Eiffert et al. |
| 2002/0169636 A1 | * | 11/2002 | Eggers et al. ..................... 705/3 |

FOREIGN PATENT DOCUMENTS

| WO | WO 02/11049 A2 | * | 2/2002 |
| WO | WO 02/069099 A2 | * | 9/2002 |
| WO | WO 03/092769 A2 | * | 11/2003 |
| WO | WO 2004061745 | | 7/2004 |

OTHER PUBLICATIONS

Japanese Office Action dated Mar. 1, 2011 from related Japanese App. No. 2007-523887.

* cited by examiner

*Primary Examiner* — Sathyanarayan Pannala
(74) *Attorney, Agent, or Firm* — McDermott Will & Emery LLP

(57) ABSTRACT

A system and method for creating, managing and loading selected configuration datasets used to program a patient care device to have a selected behavior is provided. A common configuration database includes medical treatment guidelines and device operating characteristics for a plurality of patient care device types. A processor operatively connected to the configuration database is programmed to construct at least one device-specific configuration dataset for a selected device behavior from the common configuration database and load the device-specific dataset into the memory of a patient care device. Further, the device-specific configuration datasets may contain device communication information, including communication protocols and data structures, for a plurality of patient care devices types and behaviors to enable communication between patient care devices.

8 Claims, 9 Drawing Sheets

SYSTEM AND METHOD FOR MANAGING MEDICAL DATABASES FOR PATIENT CARE DEVICES

FIELD OF THE INVENTION

The present invention relates generally to systems and methods for managing patient care in a health care facility, and more particularly, to systems and methods for creating, managing and a universal, user-specified configuration database for the purpose of customizing the behavior of a plurality of diverse patient care devices.

BACKGROUND OF THE INVENTION

Medication errors, that is, errors that occur in the ordering, dispensing, and administration of medications, regardless of whether those errors caused injury or not, are a significant consideration in the delivery of healthcare in the institutional setting. Adverse drug events ("ADE"), defined as injuries involving a drug that require medical intervention, and representing some of the most serious medication errors, are responsible for a number of patient injuries and death. Accordingly, healthcare facilities continually search for ways to reduce the occurrence of medication errors.

Various systems and methods are being developed at present to reduce the frequency of occurrence and severity of preventable adverse drug events ("PADE") and other medication errors. In the administration of medication, focus is typically directed to the following five "rights" or factors: the right patient, the right drug, the right route, the right amount, and the right time. Systems and methods seeking to reduce ADE's and PADE's should take these five rights into consideration.

In many hospitals and clinical laboratories, a bracelet device having the patient's identification, such as his or her name printed thereon, is affixed to a patient upon admittance to the facility in order to identify the patient during his or her entire stay. Despite this safeguard, opportunities arise for patient identification error. For example, when a blood sample is taken from a patient, the blood sample must be identified by manually transcribing the patient's name and other information from the patient's identification bracelet. In transferring the patient's name, a nurse or technician may, instead of actually reading the patient's bracelet, miscopy the name or may rely on memory or a different data source. Moreover, manually transferring other information such as parameters for configuring an infusion pump to dispense medication may result in errors that reduce the accuracy and/or effectiveness of drug administration and patient care. This may result in an increased duration of treatment with an attendant increase in cost.

Hospitals and other healthcare institutions continuously strive to provide quality patient care. The possibility of medical errors, such as where the wrong patient receives the wrong drug at the wrong time, in the wrong dosage, or even where the wrong surgery is performed, is a significant concern for all healthcare facilities. Many prescription drugs and injections are identified merely by slips of paper on which the patient's name and identification number have been hand-written by a nurse or technician who is to administer the treatment. For a variety of reasons, such as the transfer of patients to different beds and errors in marking the slips of paper, the possibility arises that a patient may be given an incorrect treatment. This could be prevented by using an automated system to verify that the patient is receiving the correct care. Various solutions to these problems have been proposed, such as systems that use bar codes to identify patients and medications, or systems allowing the bedside entry of patient data. While these systems have advanced the art significantly, even more comprehensive systems could prove to be of greater value.

Delivery, verification, and control of medication in an institutional setting have traditionally been areas where errors can occur. In a typical facility, a physician enters an order for a medication for a particular patient. This order may be handled either as a simple prescription slip, or it may be entered into an automated system, such as a physician order entry ("POE") system. The prescription slip or the electronic prescription from the POE system is routed to the pharmacy, where the order is filled, so that the medication can be provided to the patient. Typically, pharmacies check the physician order against possible allergies of the patient and for possible drug interactions in the case where two or more drugs are prescribed, and also check for contraindications. Depending on the facility, the medication may be identified and gathered within the pharmacy and placed into a transport carrier for transport to a nurse station. Once at the nurse station, the prescriptions are again checked against the medications that have been identified for delivery to ensure that no errors have occurred.

Typically, medications are delivered to a nurse station in a drug cart or other carrier that allows a certain degree of security to prevent theft or other loss of medications. In one example, the drug cart or carrier is divided into a series of drawers or containers, each container holding the prescribed medication for a single patient. To access the medication, the nurse must enter the appropriate identification to unlock a drawer, door, or container. In other situations, inventories of commonly-used drugs may be placed in a secure cabinet located in an area at or close by a nurse station. This inventory may contain not only topical medications but oral, IM-, and IV-delivered medications as well. Nurse identification and a medication order number are typically required to gain access to the cabinet.

The nurse station receives a listing of drugs to be delivered to patients at intervals throughout the day. A nurse or other care-giver or other qualified person reads the list of medications to be delivered, and gathers those medications from the inventory at the nurse station. Once all of the medications have been gathered for the patients in the unit for which the nurse station is responsible, one or more nurses then take the medications to the individual patients and administer the dosages.

Common to all of these systems is the nurse who delivers the medication. The nurse is central to the process of verifying that the right medication is given to the right patient in the right dosage at the right time at the point of care. No other person in the facility is situated as well as the nurse delivering the medication to ensure or verify that the appropriate drug is being given to the appropriate patient.

Such a system though may not be capable of thoroughly verifying that the appropriate medication regimen is being delivered to a patient in the case where IV drugs are being delivered. For example, a nurse may carry an IV bag to a particular patient area, hang the bag, program an infusion pump with appropriate treatment parameters, and begin infusion of the medication. The applicable hospital control system, such as the pharmacy information system, may not be informed that the patient has received the medication, and if the information is lost somewhere, the possibility exists of medicating the patient twice. Thus, there may be a break in the link of verification that the medication is being properly delivered to the patient if an event occurs resulting in a deviation from the desired treatment parameters.

Moreover, even where the right medication arrives at the right patient for administration, incorrect administration of the medication may occur where the medication is to be administered using an automated or semi-automated administration device, such as an infusion pump, if the automated device is programmed with incorrect medication administration parameters. For example, even where the medication order includes the correct infusion parameters, those parameters may be incorrectly entered into an infusion pump, causing the infusion pump to administer the medication in a manner that may not result in the prescribed treatment.

One attempt at providing an infusion system with built-in safeguards to prevent the incorrect entry of treatment parameters utilizes hospital-defined drug dosing parameters which are employed by the infusion instrument's software to monitor the infusion parameter entry process and interact with the care-giver should an incorrect entry or an out of range entry be attempted. In such a case, an alert is communicated to the care-giver that the parameter entered is either incorrect or outside of a range established by the institution where care is being provided. The drug dosing parameters consist of hospital-defined values for infusion parameters or other medical treatment guidelines. They may comprise the considered "best practices" of the facility and may be updated from time to time.

Typically, the drug dosing parameters are installed in the device by qualified personnel. However, each type (model) of infusion pump has its own independent software for creating and installing customized drug parameters for that type and model of pump. Thus, the qualified personnel must repeat the customization process for each type of infusion pump used at the institution. Further, each time the institution's guidelines or policies are updated, the drug dosing parameters for each type of infusion pump must be separately updated as well.

In the case of modular systems having a single programming module that controls multiple infusion pumps or infusion pump modules, such as in ALARIS Medical Systems, Inc.'s MEDLEY® Modular Patient Care System, the drug dosing parameters are installed in the programming module, or common Patient Care Unit™ (PCU), and are thereby usable by all the infusion modules attached to the "system". However, even with this modular system, the customizable drug dosing parameters are limited to use with that particular model. Further, they can only be installed in that model's Patient Care Unit™ (programming module) and not other models or devices manufactured by ALARIS and certainly not the devices of other manufacturers.

While these hospital-defined drug dosing parameters have provided a significant advance in the art for avoiding medication errors, when more than one model of patient care device is used by a hospital, the process for customizing separate databases for each device model requires a significant amount of time by skilled personnel and introduces a risk of inconsistency. Therefore, it would be advantageous to provide a more accurate and efficient system to create and deploy hospital-defined drug dosing parameters and rules for different models of infusion devices as well as other patient care devices. It would also be advantageous for hospitals as well as manufacturers to be able to develop and implement a single customizable set of drug dosing parameters and rules which may be applied to all the infusion devices and associated monitoring and diagnostic devices and systems in the hospital.

In some cases, diverse types or models of patient care devices may need to communicate with each other for purposes of sharing information. For instance, patient monitoring devices such as vital signs monitors often have the capability of storing transactions from other patient care devices, such as infusion pumps. These monitoring devices typically require the parameters of the other patient care devices so that appropriate correlation, labeling, data validation and storage functions may be provided. Additionally, in cases where the drug dosing parameters further include rule sets representing patient-condition-specific rules and/or algorithms that determine dosing parameter(s) as a function of patient data obtained from other sources in the network, information from one device may be essential to another device that is utilizing the hospital's drug dosing parameters. Further, some devices may alter operation in response to the information received from another device, either in accordance with a drug dosing rule or other operational software in the system or device. For example, the rule for maximum and minimum dose of sodium nitroprusside can be made dependent on the arterial blood pressure measured by a separate instrument. If the mean blood pressure exceeds a predetermined limit or meets a certain categorization such as "high", then the dosing parameter defining the upper continuous dose limit would be reduced in accordance with the parameters of the dosing rule for that drug within a selected behavior descriptor, as that term will be defined below.

However, each healthcare facility typically has a different inventory of diverse models of patient care devices, many of which are not compatible with each other because they are made by different manufacturers or are otherwise supported by different platforms that use different languages and/or communication protocols to transmit or receive data. Thus, it would be advantageous to provide a universal configuration database from which these diverse devices could easily obtain the needed communication information (e.g. data definitions, rules, protocols, structures, definitions) to support communication with other types of patient care devices. It would also be advantageous if such a system was integrated with the customizable drug dosing parameters and rules as well as the infusion/monitoring instrument's operational configuration parameters.

The operational behavior of many infusion devices are capable of being customized through installation of "configurable operation parameters" including such parameters as alarm limits, maximum rates, selection of operational modes and languages. Depending on the type of infusion device and area in which the device is used, specific settings are needed to provide optimal care. For instance, the neonatology department will prefer a low rate limit, the smallest air bubble detection limit and special settings for pressure and resistance alarms.

For example, many infusion pumps presently available allow users to determine the behavior of the medical device by choosing one of a list of behaviors referred to as "profiles". The parameters of each "profile" are defined generically as behavior descriptors, the elements of which are selected to provide optimal behavior of the medical device in a specific care area (ICU, OR, etc) or type of medical care (cardiology, oncology). By the operator's selection of a "profile", the infusion pump or other medical device becomes automatically customized to provide optimal operating features for the patient's in the selected care area. For example, both infusion devices and vital signs monitoring modules may be combined in a single integrated patient care system controlled by a central computer referred to as a PCU. The operational behaviors of monitoring modules include features such as alarm limits and display range. Similar to infusion modules, the behavior of these devices may be customized through the selection of the desired "profile" or ensemble of operating parameters.

A need therefore exists for a hospital-specified configuration database to coordinate all the above features, functions, rules and communication parameters. This "universal" configuration database will integrate individualized infusion device and monitoring device operational parameters together with drug infusion parameters and rules. Hence what has been recognized as a need, and has heretofore been unavailable, is an integrated system for creating and managing customized institutional guidelines for medical treatments usable with a variety of patient care devices to provide accurate, efficient, and cost-effective delivery of health care to patients. Such a system should also be capable of facilitating communication between heterogeneous patient care devices for further integrating the various aspects of patient care such as the operational parameters of infusion devices and monitors. The invention fulfills these needs and others.

SUMMARY OF THE INVENTION

Briefly, and in general terms, the present invention is directed to a new and improved information management system and method capable of creating, managing and controlling a hospital-defined universal configuration database for patient care devices at a healthcare facility.

The following definitions of terms are intended to apply in this document: "Universal Configuration Database means a user (or institutionally) defined file consisting of electronically stored set of information used to customize the function of a plurality of medical devices and/or systems including, but not limited to operating configuration parameters, such as, for example, infusion pump pressure limits, communication rules and methods such as, for example, communication protocol, baud rate, IP addresses, etc., therapeutic device or system rules, including medication delivery rules such as, for example, infusion dose limits, dose units, maximum and minimum flow rates and the like, and monitoring device or system rules, such as, for example, alarm limits and parameters such as range, repetition interval and the like. Elements of the universal configuration database are selectable and installable into various medical devices and systems in order to provide systematic, uniform operation customized to the requirements of the medical institution and to facilitate exchange of information between diverse sources and repositories of information. A selection of appropriate "elements" of the universal configuration database is herein called a "dataset." The term "Ensemble" is defined to mean a subset of the configuration parameters discussed above defining a distinct behavior or the device or system. Selection of a desired ensemble places the parameters associated with that ensemble in the "dataset." The various operating parameters or rules sets that may be selected to be included in a dataset are also defined herein as "behavior descriptors" because they determine the behavior of the medical device into which they are installed. Thus, the term "dataset" may also be described as a "behavior structure."

In one aspect, the present invention comprises a plurality of patient care devices capable of being programmed to operate in accordance with a specific behavior, each device including a memory for storing at least one device-specific configuration dataset for controlling the patient care device in accordance with the specific behavior, a universal configuration database containing operating information for a plurality of device behaviors, a processor operatively connected to the universal configuration database and configured to load at least one device-specific configuration dataset associated with a selected device behavior into the memory of at least one of the patient care devices to program the at least one patient care device in accordance with the operating information contained in the device-specific dataset, and a communication system operatively connecting each of the plurality of devices to the processor.

In another aspect, the patient care system of the present invention includes an embodiment wherein each specific behavior corresponds to a different infusion pump system, and also wherein the operating information includes medical treatment guidelines and/or device operating characteristics.

In still another aspect, the patient care system of the present invention comprises a system wherein the operating information further includes communication protocols and data structures for a plurality of types of patient care devices to enable communication between the types of patient care devices, and/or wherein the processor is configured to load a plurality of device-specific configuration datasets into the memory of one of the patient care devices, and each of the device-specific configuration datasets includes a plurality of device operating parameters representing the medical treatment guidelines. In a further aspect, the system of the present invention may also comprise means for activating one of the loaded device-specific configuration datasets to program the patient care device to operate in accordance with a desired behavior in response to patient-specific information communicated to the patient care device.

In yet a further aspect, the present invention comprises a patient care system including a plurality of patient care devices each having a memory for storing at least one device-specific configuration dataset, a configuration database containing operating information including medical treatment guidelines and device operating characteristics associated with a plurality of a plurality of device behaviors, editing means for editing the medical treatment guidelines, wherein the medical treatment guidelines that are common to multiple device behaviors are automatically edited for each of the corresponding device behaviors, and loading means for selectively loading at least one device-specific configuration datasets into at least one of the patient care devices in accordance with a desired device behavior.

In a still further aspect, the present invention comprises a system for creating device-specific configuration datasets for each of a plurality of desired device behaviors including a common configuration database containing medical treatment guidelines and device operating characteristics for a plurality of device behaviors, and a processor operatively connected to the common configuration database and configured to construct a device-specific configuration dataset for a selected device behavior from the common configuration database and load the device-specific dataset into a memory of at least one patient care devices to control the patient care device in accordance with the selected device behavior.

In another aspect, the present invention comprises a patient care system comprising a plurality of patient care devices having a memory for storing a configuration dataset and a first processor configured to operate the patient care device in accordance with the stored configuration dataset, a common configuration database in which is stored device communication information comprising communication protocols and data structures for a plurality of types of patient care devices, a second processor operatively connected to the common configuration database and configured to load the database into the memory of a selected patient care device to enable communication between the selected patient care device and other patient care devices representing different device types than the selected patient care device, and a network operatively connecting each of the plurality of devices to the second processor.

In still another aspect, the present invention includes a method for creating device-specific configuration dataset for each of a plurality of device types comprising the steps of storing operating information representing a plurality of patient care device behaviors in a common configuration database, wherein the operating information includes medical treatment guidelines, each guideline including a plurality of device operating parameters for programming a patient care device to have a selected behavior, editing the device operating parameters for the medical treatment guidelines, wherein the parameters that are common to multiple device behaviors are automatically edited for each of the corresponding device behaviors, constructing at least one device-specific configuration dataset from the common configuration database, the device-specific configuration database including only the medical information from the common configuration database associated with a selected device behavior, and loading the at least one device-specific configuration dataset into a memory of a patient care device.

In a further aspect, the present invention comprises a system for recognizing medical treatment devices and for loading device specific information into a recognized medical treatment device to configure the device comprising a communication module for establishing communication with a medical treatment device, a recognition module configured to query the medical treatment device and determine an identification of the medical treatment device, and a loading module configured to communicate with the medical treatment device, to construct a dataset from a plurality of stored datasets in accordance with the identification of the medical treatment device and to communicate the constructed dataset to the medical treatment device and load the dataset into the medical treatment device to configure the medical treatment device.

Other features and advantages of the invention will become apparent from the following detailed description, taken in conjunction with the accompanying drawings, which illustrate, by way of example, the features of the invention.

DETAILED DESCRIPTION OF THE PREFERRED EMBODIMENTS

The present invention provides a system and method for creating, managing and installing a universal configuration database or portions thereof and using this database to customize the behavior of patient care devices and systems in a healthcare facility according to the specifications of that facility. Additionally, the universal configuration database provides rules and parameters to facilitate communication between diverse patient care devices from multiple manufacturers.

Digital Communication Network

Figure 1:
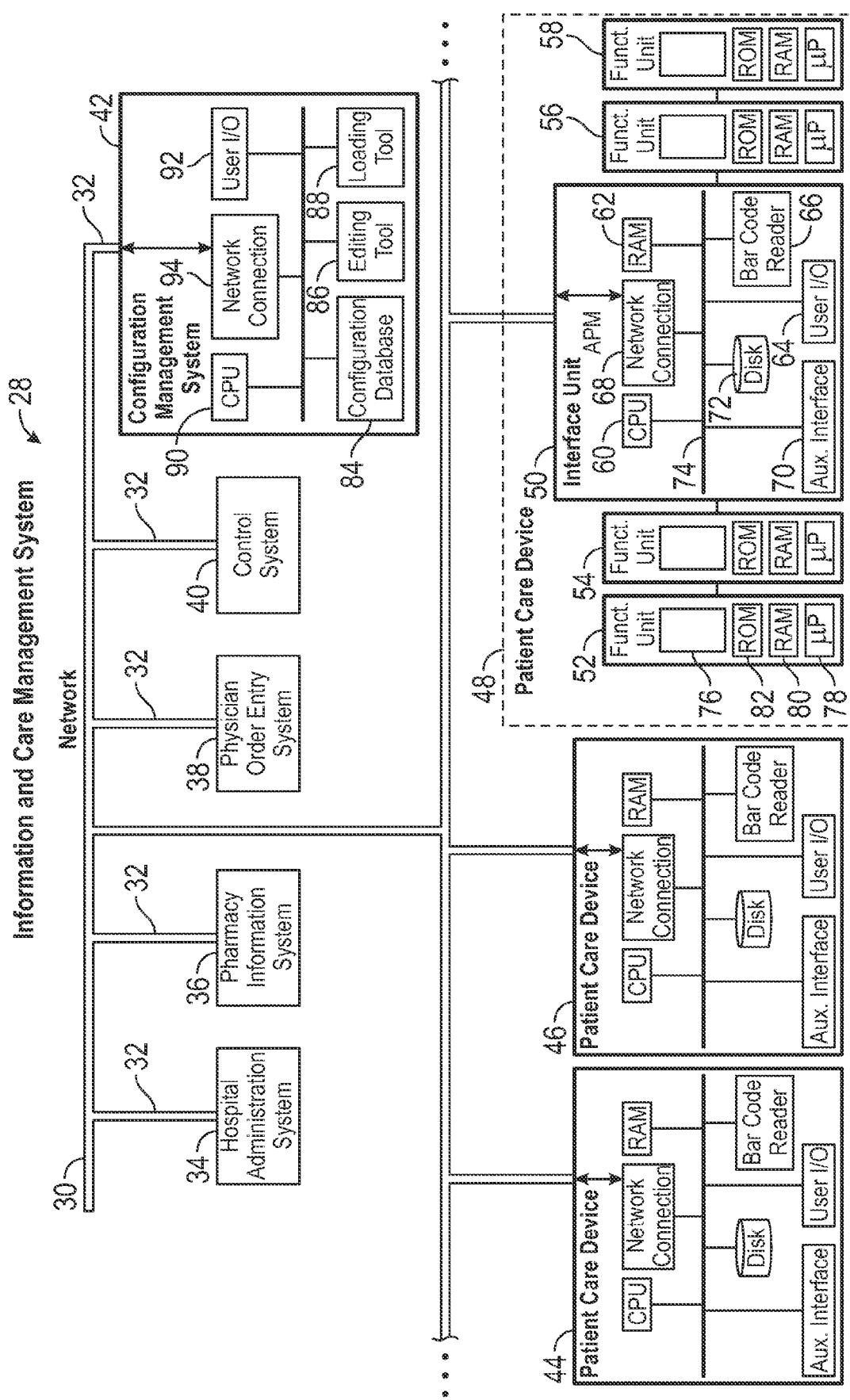
FIG. 1 is a schematic diagram of a hospital-wide information and care management system incorporating principles of the present invention.

Referring now to drawings in which like reference numerals are used to refer to like or corresponding elements among the figures, there is generally shown in FIG. 1 an integrated hospital-wide information and care management system 28 in accordance with aspects of the present invention. Various subsystems of the facility's information and care management system are connected together by way of a communication system 30. The communication system 30 may be, for example, a local area network (LAN), a wide area network (WAN), Inter- or intranet based, or some other communication network designed to carry signals allowing communications between the various information systems in the facility. For example, as shown in FIG. 1, the communication system 30 connects, through various interfaces 32, a hospital administration system 34, a pharmacy information system 36, a physician order entry (POE) system 38, a control system 40, and a configuration management system 42. A plurality of patient care devices or systems 44, 46 and 48 may also be connected to communication system 30.

The communication system 30 may comprise, for example, an Ethernet (IEEE 522.3), a token ring network, or other suitable network topology, utilizing either wire or optical telecommunication cabling. In an alternative embodiment, the communication system 30 may comprise a wireless system, utilizing transmitters and receivers positioned throughout the care-giving facility and/or attached to various subsystems, computers, patient care devices and other equipment used in the facility. In such a wireless system, the signals transmitted and received by the system could be radio frequency (RF), infrared (IR), or other means capable of carrying information in a wireless manner between devices having appropriate transmitters or receivers. It will be immediately understood by those skilled in the art that such a system may be identical to the system set forth in FIG. 1, with the exception that no wires are required to connect the various aspects of the system.

Each of the various systems 34, 36, 38, 40 and 42 generally comprise a combination of hardware such as digital computers which may include one or more central processing units, high speed instruction and data storage, on-line mass storage of operating software and short term storage of data, off-line long-term storage of data, such as removable disk drive platters, CD ROMs, or magnetic tape, and a variety of communication ports for connecting to modems, local or wide area networks, such as the network 30, and printers for generating reports. Such systems may also include remote terminals including video displays and keyboards, touch screens, printers and interfaces to a variety of clinical devices. The processors or CPUs of the various systems are typically controlled by a computer program or programs for carrying out various aspects of the present invention, as will be discussed more fully below, and basic operational software, such as a Windows™ operating system, such as Windows NT™, or Windows 2000™, or Windows XP™, distributed by Microsoft, Inc., or another operating program distributed, for example, by Linux, Red Hat, or any other suitable operating system. The operational software will also include various auxiliary programs enabling communications with other hardware or networks, data input and output and report generation and printing, among other functions.

Modular Patient Care Device

Patient care devices and systems 44, 46 and 48 may comprise a variety of diverse medical devices including therapeutic instruments such as parenteral and enteral infusion pumps and respirators, physiological monitors such as heart rate, blood pressure, ECG, EEG, and pulse oximeters, and clinical laboratory biochemistry instruments such as blood, urine and tissue sample measurement instruments and systems.

In one embodiment, the patient care device 48 comprises a modular system similar to that described in U.S. Pat. No. 5,713,856 to Eggers et al., which is incorporated herein by reference. In this embodiment, the patient care device 48 comprises an advanced programming module 50, also referred to as interface unit 50, connected to one or more functional modules 52, 54, 56, 58. Interface unit 50 includes a central processing unit (CPU) 60 connected to a memory, e.g. random access memory (RAM) 62, and one or more interface devices such as user interface device 64, a data input device 66, a network connection 68, and an auxiliary interface 70 for communicating with additional modules or devices. Interface unit 50 also preferably, although not necessarily, includes a main non-volatile storage unit 72, preferably a hard disk drive, for storing software and data and one or more internal buses 74 for interconnecting the aforementioned elements. As shown in FIG. 1, patient care devices 44, 46 may represent single-module patient care devices that include the same components as the interface unit 50.

In a typical embodiment, user interface device 64 is a touch screen for displaying information to a user and allowing a user to input information by touching defined areas of the screen. Alternatively, user interface device 64 could include any means for displaying and inputting information, such as a monitor, a printer, a keyboard, softkeys, a mouse, a track ball and/or a light pen. Data input device 66 is preferably a bar code reader capable of scanning and interpreting data printed in bar coded format. Alternatively, data input device 66 could be any device for entering data into a computer, such as devices for reading magnetic strips, PCMCIA smart cards, radio frequency cards, RFID tags, memory sticks, CDs, DVDs, or any other analog or digital storage media. Other examples of data input device 66 include a voice activation or recognition device or a portable personal data assistant (PDA). Depending upon the types of interface devices used, user interface device 64 and data input device 66 may be the same device. Alternatively, although data input device 66 is shown in FIG. 1 to be disposed within interface unit 50, one skilled in the art will recognize that data input device 66 may be integral within pharmacy information system 36 or located externally and communicating with pharmacy information system 36 through an RS-232 serial interface or any other appropriate communication means. Auxiliary interface 70 is preferably an RS-232 communications interface, however any other means for communicating with a peripheral device such as a printer, patient monitor, infusion pump or other patient care device may be used without departing from the scope of the invention.

Digital Communication Methods

Network connection 68 is preferably a direct network connection such as a T1 connection, an integrated services digital network (ISDN) connection, a digital subscriber line (DSL) modem or a cable modem. Alternatively, any direct or indirect network connection may be used, including, but not limited to a telephone modem, an MIB system, an RS232 interface, an auxiliary interface, an optical link, an infrared link, a radio frequency link, a microwave link or a WLANS connection.

Modular Patient Care Devices

Functional modules 52, 54, 56, 58 are any patient care devices under the immediate control of the interface unit 50, for providing care to a patient or for monitoring patient condition. In one embodiment of the present invention, at least one of functional units 52, 54, 56, 58 is an infusion pump module such as an intravenous infusion pump for delivering medication or other fluid to a patient. For the purposes of this discussion, functional unit 52 is an infusion pump module. Each of functional units 54, 56, 58 may be any therapeutic or monitoring device including, but not limited to, an infusion pump module, a syringe infusion module, a Patient Controlled Analgesia (PCA) module, an epidural infusion module, an infusion module pump, a blood pressure monitor, a pulse oximeter, an EKG monitor, an EEG monitor, an end-tidal $CO_2$ ($etCO_2$), a heart rate monitor or an intracranial pressure (ICP) monitor. Alternatively, functional module 54, 56 and/or 58 may be a printer, scanner or any other peripheral input/output or communication device.

Each functional unit 52, 54, 56, 58 communicates directly or indirectly with interface unit 50, which provides overall control and display of the status of modular patient care device 48. In one embodiment, functional units 52, 54, 56, 58 are connected physically and electronically in serial fashion to one or both ends of interface unit 50 as shown in FIG. 1 and as detailed in Eggers et al. However, one skilled in the art will recognize that there are other means for connecting functional modules with the interface unit which may be utilized without departing from the scope of the invention. It will also be appreciated that devices such as pumps or monitors that provide sufficient programmability and connectivity may communicate directly with the network without a separate interface unit. As described above, additional medical devices or peripheral devices may be connected to patient care system 48 through one or more auxiliary interfaces 70.

Each functional unit 52, 54, 56, 58 typically includes module-specific components 76, a microprocessor 78, a volatile memory 80 and a nonvolatile memory 82 for storing information. It should be noted that while four functional modules are shown in FIG. 1, any number of devices may be connected directly or indirectly to central computer 50. The number and type of functional modules described herein are intended to be illustrative, and in no way limit the scope of the present invention. Module-specific components 76 include any components necessary for operation of a particular module, such as, for example, a pumping mechanism for infusion pump module 52.

While each functional unit is typically capable of a least some level of independent operation, interface unit 50 monitors and controls overall operation of modular patient care device 48. For example, as will be described in more detail below, interface unit 50 provides programming instructions and power to the functional unit 52, 54, 56, 58 and monitors the status of each module receiving data for both display, coordination of control of other modules and for communication to connected medical devices and information systems.

Universal Configuration Database

According to one embodiment of the present invention, patient care devices and systems 44, 46, 48 are capable of being customized through installation of data, rules and operating parameters derived from a universal configuration database containing institutionally-established guidelines for medical treatments, such as a drug dosing parameters and rules, device operating characteristics and communication parameters. Each of the patient care devices or system 44, 46, 48 may comprise a different device type having at least some of its own distinct device operating characteristics or features.

The following definitions of terms are intended to apply in this document: "Universal Configuration Database means a user (or institutionally) defined file consisting of electronically stored set of information used to customize the function of a plurality of medical devices and/or systems including, but not limited to operating configuration parameters, such as, for example, infusion pump pressure limits, communication rules and methods such as, for example, communication protocol, baud rate, IP addresses, etc., therapeutic device or system rules, including medication delivery rules such as, for example, infusion dose limits, dose units, maximum and minimum flow rates and the like, and monitoring device or system rules, such as, for example, alarm limits and parameters such as range, repetition interval and the like. Elements of the universal configuration database are selectable and installable into various medical devices and systems in order to provide systematic, uniform operation customized to the requirements of the medical institution and to facilitate exchange of information between diverse sources and repositories of information. A selection of appropriate "elements" of the universal configuration database is herein called a "dataset." The term "Ensemble" is defined to mean a subset of the configuration parameters discussed above defining a distinct behavior or the device or system. Selection of a desired ensemble places the parameters associated with that ensemble in the "dataset." The various operating parameters or rules sets that may be selected to be included in a dataset are also defined herein as "behavior descriptors" because they determine the behavior of the medical device into which they are installed. Thus, the term "dataset" may also be described as a "behavior structure."

A device type, for example, may represent a distinct brand, model, platform or manufacturer of a patient care device. Two different infusion pump systems which perform the same or similar functions may represent different device types where they are physically and functionally separate and distinct systems or platforms, either from the same or different manufacturer. Different device types may also be incompatible with each other in terms of communicating with each other for purposes of sharing data within a health care facility.

The BEHAVIOR DESCRIPTOR elements of the device specific dataset installed in a patient care device, either in a memory of the device or in some other storage media accessible by the device or a processor controlling the device, will only be those specific for that type of device. Other information installed in the device or system may include infusion dosing parameters and rules, dose sequencing, and communication parameters.

The device-specific datasets are created by the configuration management system 42 which, as shown in FIG. 1, includes a universal configuration database 84 containing configuration data and parameters for a plurality of diverse device and system types. For example, the universal configuration database may contain medication delivery parameters such as drug infusion parameters and rules and device operating characteristics for a plurality of diverse device types. An editing tool 86 permits qualified personnel such as a biotechnical engineer at the institution, to customize the universal configuration database to include the institution's accepted values for the various parameters in the guidelines.

An installation tool 88 facilitates transfer of appropriate portions of the universal configuration database into each device or system according to its type. In this way, device or system-specific datasets are created and loaded into the appropriate patient care devices or systems. Both the universal configuration database editing tool 86 and the installation tool 88 may be embodied in software applications executing on a CPU 90 associated with the configuration management system 42.

The user may interact with the system for editing database elements or for creating media for use in carrying out the installation of a configuration. This may be performed using interface device 92, which may be a printer, floppy disc drive, CD writer, bar code writer, EPROM writing device or any other media appropriate for transfer of a configuration. In the case that the hospital has available a digital communication network with which medical devices (also referred to as clinical devices) and systems are in communication, the configuration management system 42 may include a network connection 94 for installing the device-specific configuration into the patient care devices via the communication system 30.

In one embodiment of the present invention, one or more of the patient care devices or systems 44, 46, 48 is capable of operating in one of several selectable modes with each mode defined by the universal configuration database. Thus, the universal configuration database 84 may contain multiple elements for a plurality of patient care devices and facilitate installation of the selected mode in accordance with the device type. These particular elements define a behavior of the pump that may be changed as necessary depending on the environment in which the device is being used, patient specific information, medications or other therapeutic agents to be delivered, or vital signs or laboratory results being monitored. A particular behavior stored in a patient care device is selected based, at least in part, by patient-specific information such as patient location, age, physical characteristics, or medical characteristics. Medical characteristics include, but are not limited to, patient diagnosis, treatment prescription, medical history, medical records, patient care provider identification, physiological characteristics or psychological characteristics. As used herein, patient-specific information may also include care provider information (e.g., physician identification) or a patient care device's location in the hospital or hospital computer network. Patient care information may be entered through interface device 64, 66, 68 or 70, and may originate from anywhere in network 30, such as, for example, from the hospital administration system 34, pharmacy information system 36, physician order entry system, or any other system or department in the facility.

Data to and from the various data sources can be converted into network-compatible data with existing technology, and movement of the information between the medical device and network can be accomplished by a variety of means. For example, patient care devices or systems 44, 46, 48 and the network may communicate via automated interaction and/or manual interaction. Automated interaction may be continuous or intermittent and may occur through direct network connection 68 (as shown in FIG. 1), or alternatively through RS232 links, MIB systems, RF links such as BLUETOOTH (Amtel Corp., San Jose, Calif.), IR links, WLANS, digital cable systems, telephone modems or other communication means. Manual interaction between patient care devices or systems 44, 46, 48 and the network involves physically transferring, intermittently or periodically, data between systems using, for example, user interface device 64, data input device 66, bar codes, computer disks, portable data assistants, memory cards, or any other media for storing data. Preferably, the communication means is bidirectional with access to data from as many points of the distributed data sources as possible. Decision-making can occur at a variety of places within the network. For example, and not by way of limitation, decisions can be made in hospital administration system 34, pharmacy information system 36, other departments or systems such as a nursing station or a bedside CPU, or within patient care device or system 44, 46 or 48 itself.

Figure 2:
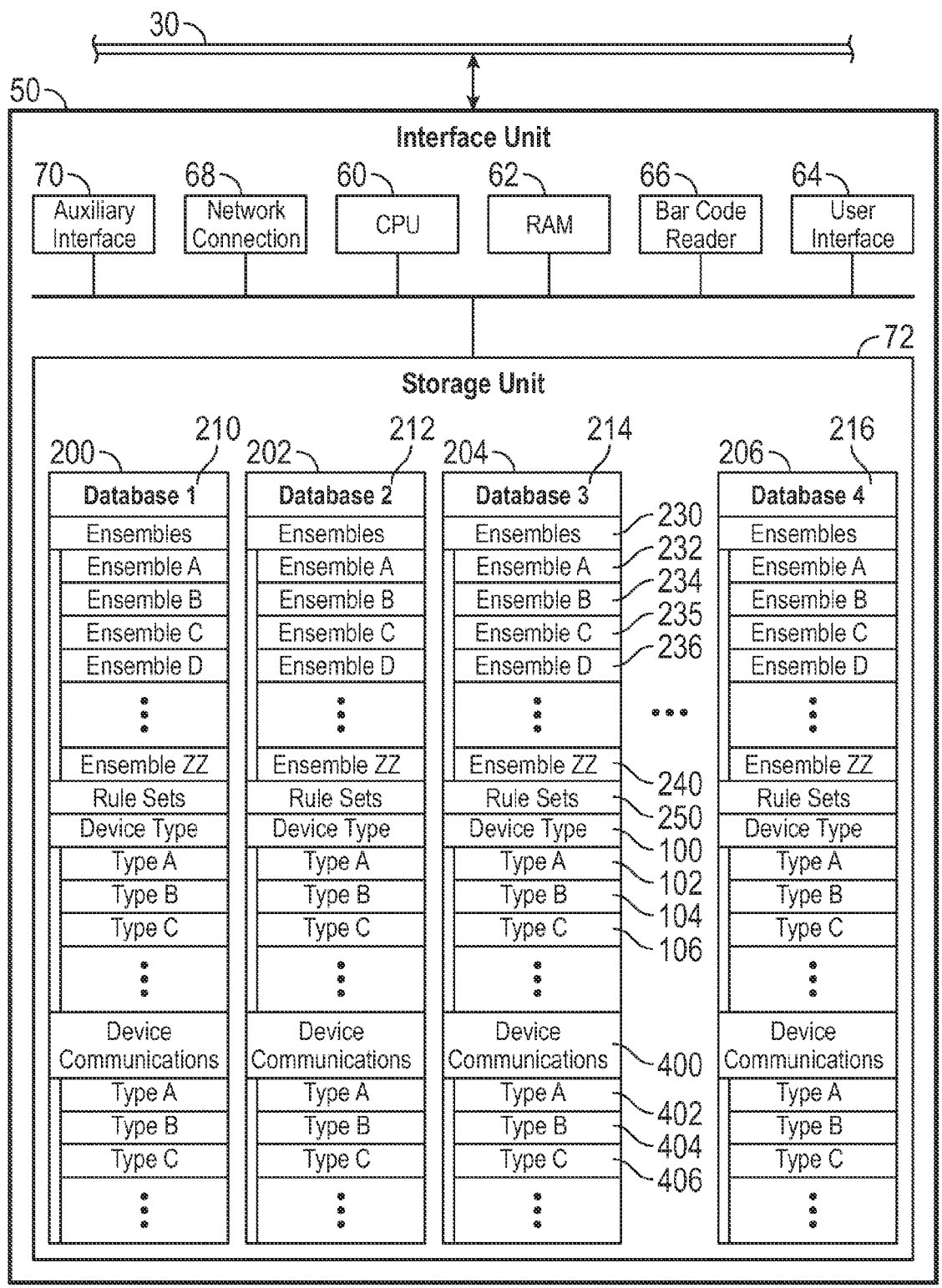
FIG. 2 is a schematic diagram of an interface unit and the contents of its memory, including a diagram of a universal configuration database, according to aspects of the present invention.

Referring to FIG. 2, in one embodiment of the present invention, the universal configuration database 84 includes one or more components containing available treatment protocols, drug library information, rule sets, device operating characteristics such as device or module operating limits and device features, and possibly other information for defining particular operating parameters for a plurality of types of patient care devices. At least a portion of the database contains information that is specific for each type of device. As shown in FIG. 2, Device Type module 100 in the database 84 contains device-specific information for Device Types A, B and C identified by reference numerals 102, 104 and 106, respectively. While three devices types are depicted in FIG. 2, more or fewer types of devices may be supported by the database. The fields for each Device Type 102, 104, 106 contain the information specific for each device type, such as device operating characteristics, as will be described in more detail below.

Installation of a Dataset

Figure 3:
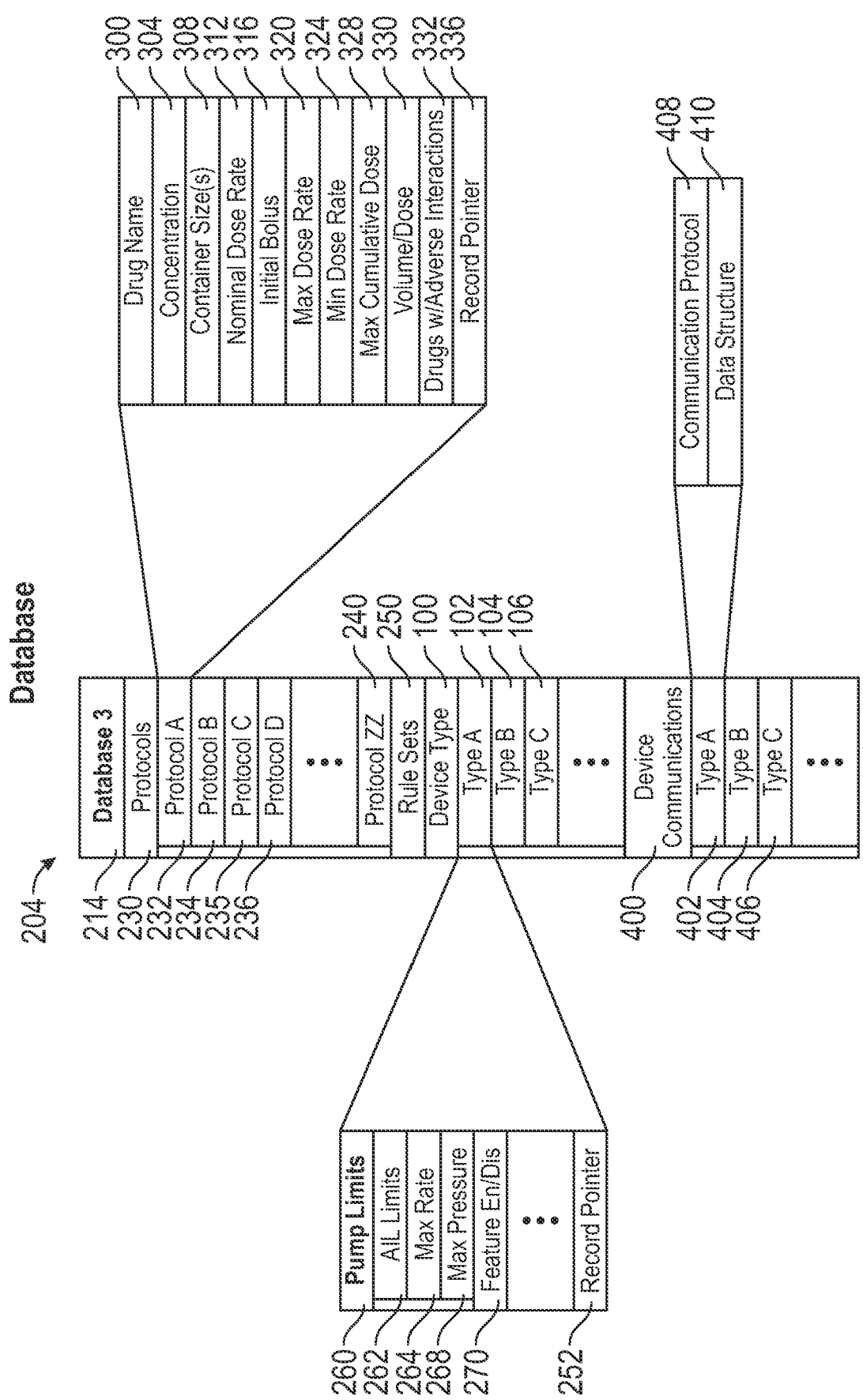
FIG. 3 is a schematic diagram illustrating more detailed aspects of a universal configuration database according aspects of to the present invention.

The universal configuration database 84 may also include components defining a plurality of datasets 200, 202, 204 and 206 that define desired medical device or system behaviors that may be customized for each device type using the editing tool 86. Customized, device-specific configuration datasets may then be installed into patient care devices, such as interface unit 50, as shown in FIG. 3. Although this embodiment is primarily described with respect to the interface unit 50 of patient care device or system 48, it will be understood that appropriate configuration datasets may similarly be loaded into the other patient care devices 44, 46. The configuration dataset is preferably stored in memory 72 of interface unit 50, however appropriate elements of a specific device configuration dataset may be stored within a functional unit 52, 54, 56, 58 (FIG. 1). One skilled in the art will understand that, while memory 72 is preferably an internal hard disk, any permanent or removable storage media including, but not limited to, CD-ROM, EEPROM, diskette, tape, external hard disk, memory card, flash memory, etc. may be used. Optionally, portions of configuration datasets 200, 202, 204, 206 may be stored in volatile memory such as RAM 62.

Each of the configuration datasets 200, 202, 204, 206 preferably includes one or more unique behavior type identifiers, or pointers, 210, 212, 214, 216, for identifying the respective behavior that will be imparted to the functional unit when the configuration dataset is installed in the functional unit. Each configuration dataset 200, 202, 204, 206, which may also be considered to be behavior structures for determining and controlling the behavior of the medical devices or systems into which they are installed, includes a plurality of fields which define, for example, available infusion parameters and rules, device operating characteristics such as device or module operating limits and device features, and possibly other information for defining particular operating parameters for a plurality of types of patient care devices. As mentioned previously, the device-specific information may be organized in the Device Type module 100.

The individual behavior structures of a configuration dataset 200, 202, 204 and 206 typically consist of a set of operating parameters and drug dosing rules and may be treatment location specific (e.g. intensive care unit [ICU], neonatal intensive care unit [NICU], pediatrics, oncology, etc.), disease state specific (intracranial pressure management, bone marrow transplant, etc.), user specific (LPN, RN, physician, etc.), or created by any other rationale. For example, according to one embodiment of the present invention, when patient care device or system 48 is located in the ICU it utilizes behavior 200, and when device 48 is located in the NICU it utilizes behavior 202. Each behavior 200 and 202, respectively, contains particular operating parameters, treatment protocols, features, etc. that configure device or system 48 for use with patients in that unit of the hospital.

It should be noted that while FIG. 2 shows that each dataset includes the same categories and types of information, the structure of the dataset may vary considerably in terms of the types and amounts of information it contains. For devices/systems capable of multiple user-selectable behaviors, elements of the configuration dataset, when selected, at least in part define the operational behavior of the device or system 48 and includes a plurality of distinct behavior data structures.

FIG. 3 is a more detailed representation of a sample Infusate Delivery data structure 204 according to one embodiment of the present invention. Configuration database 204 includes an ensemble structure 230 comprising a plurality of ensembles 232, 234, 236, 238, 240. Each ensemble includes a plurality of fields of default operating parameters. In some cases an infusion ensemble may include a complete detailed infusion instruction with all of the default parameter values defined. Other infusion ensembles may have partially defined parameters with additional data entry required by the user at the point of care. For example, ensemble A 232 of FIG. 3 includes fields of default operating parameter values and other data for controlling a medication infusion pump. The fields of this example include drug name 300, concentration 304, container size(s) 308, default dose rate 312, default bolus 316, maximum dose rate 320, minimum dose rate 324, maximum cumulative dose 328, drug incompatibility 332 and an ID field, record pointer 336, for identifying or "calling" the specific ensemble record. Each field typically includes stored default parameter values that collectively define a specific infusion ensemble. Some fields, such as drug incompatibility 332, may also include a reference or link to a drug information library typically resident within the hospital's pharmacy computer system containing relevant information. Such references to commonly used data libraries allow data to be shared between ensembles and/or the universal configuration database to avoid duplicate storage and entry and to allow efficient updating of database information.

Alternatively, all ensembles need not be stored within each configuration dataset. Rather, ensembles from different configuration datasets may be saved in a master database or library, with each individual configuration datasets containing reference links to particular ensembles stored in the universal configuration database. Such an arrangement is advantageous because it avoids duplicate storage of identical ensembles and facilitates updating of information contained within the universal configuration database.

Following selection of a particular infusion ensemble, certain information potentially resident in other locations may be accessed. For example, device or system 48 may query a hospital communication network using the communication parameters defined (if present) to automatically obtain data such as patient weight from the patient's electronic records in hospital administration system 34, dose ordered from the computerized physician order entry system (CPOE), drug incompatibility data from a pharmacy information system 36 and clinical chemistry results which are pertinent to the infusion and referenced by the infusion ensemble rules. Additional verification of the dose and medication identity may be accomplished through access to the Medication Administration Record (MAR or eMAR) contained in the pharmacy information system 36. In the absence of a digital communication network, the user may manually enter data such as the patient weight and total dosage directly into the device or system. In one embodiment of the invention, information associated with a drug specific ensemble is automatically entered into the device or system by selection of a specific infusion ensemble. The supplied information may include, for example, the dose and flow rate limits and mode (hard limits or soft limits, or both), dose units, drug amount and diluent limits, and bolus limit. Information required to complete the dose program that was not available from the infusion ensemble data, such as patient weight, drug amount, diluent volume, dose rate and total dosage, may be manually entered through a user interface. The user interface may confirm the automatically selected parameters as prompted.

Different configuration datasets, or behavior structures, typically include different fields and/or different parameter values, within each field. Thus, Ensemble B 234 might include additional fields compared to Ensemble A 232, where the additional fields define instructions and/or parameters for implementing one or more different infusion types such as primary/secondary infusion, multichannel coordinated infusion and multidose ensembles. Alternatively, Ensemble B 234 could include the same fields as Ensemble A 232, and differ only in terms of one or more parameter values in one of the fields. For example, both ensembles could be designed to provide infusion of the drug dopamine, where one ensemble has a concentration 304 value of 400 mg/250 mL while the other has a concentration 304 value of 800 mg/250 mL.

Referring again to FIG. 4, the Rule Sets module 250 of configuration database 204 includes rules and/or algorithms that may be used to help define particular parameters within a configuration database. For example, Rule Sets module 250 could include an algorithm that modifies the maximum allowable infusion rate or some other parameter based upon data obtained from other sources in network 30, such as patient age, body weight or medical history from hospital administration system 34 or test results from the laboratory. Other rule sets in the Rule Sets module 250 may provide warnings or recommendations upon the occurrence of particular events within pump module 52, such as occlusion of the infusion line.

Still other rule sets within module 250 may contain algorithms that utilize measurements from one or more functional modules to modify operation of another functional module. For example, module 250 may contain a rule set that monitors blood pressure and intracranial pressure in a head trauma patient and calculates resulting perfusion pressure. The system then notifies the user when perfusion pressure falls outside of a defined range and recommends adjusting infusion rate of a therapeutic agent to increase blood pressure or to decrease intracranial pressure.

Together, the ensembles and rule sets generally define the accepted guidelines for appropriate medical treatment parameters established by an institution. They may include, for example, the institutionally established guidelines or limits on drug administration parameters, such as dosage, frequency of administration, and other delivery related information such as, for example, appropriate flow rates and infusion durations for programming infusion pumps. Additionally, in conjunction with the plurality of configuration databases, the protocols and rule sets may encompass guidelines for providing drug administration appropriate to particular patient treatment areas having different sets of delivery parameters for similar medications, such as medication administration directed to geriatric, pediatric and oncology patients. Guidelines may also be included that are directed to particular therapy regimens, such as chemotherapy regimens or regimens for treating chronic infection or pain. In one embodiment of the present invention, the ensembles and rule sets may include "hard" and "soft" limit values on physiological parameters (such as $CO_2$, $SpO_2$, respiration rate, and others), PCA dosing parameters, and other infusion and vital sign parameters.

Figure 4:
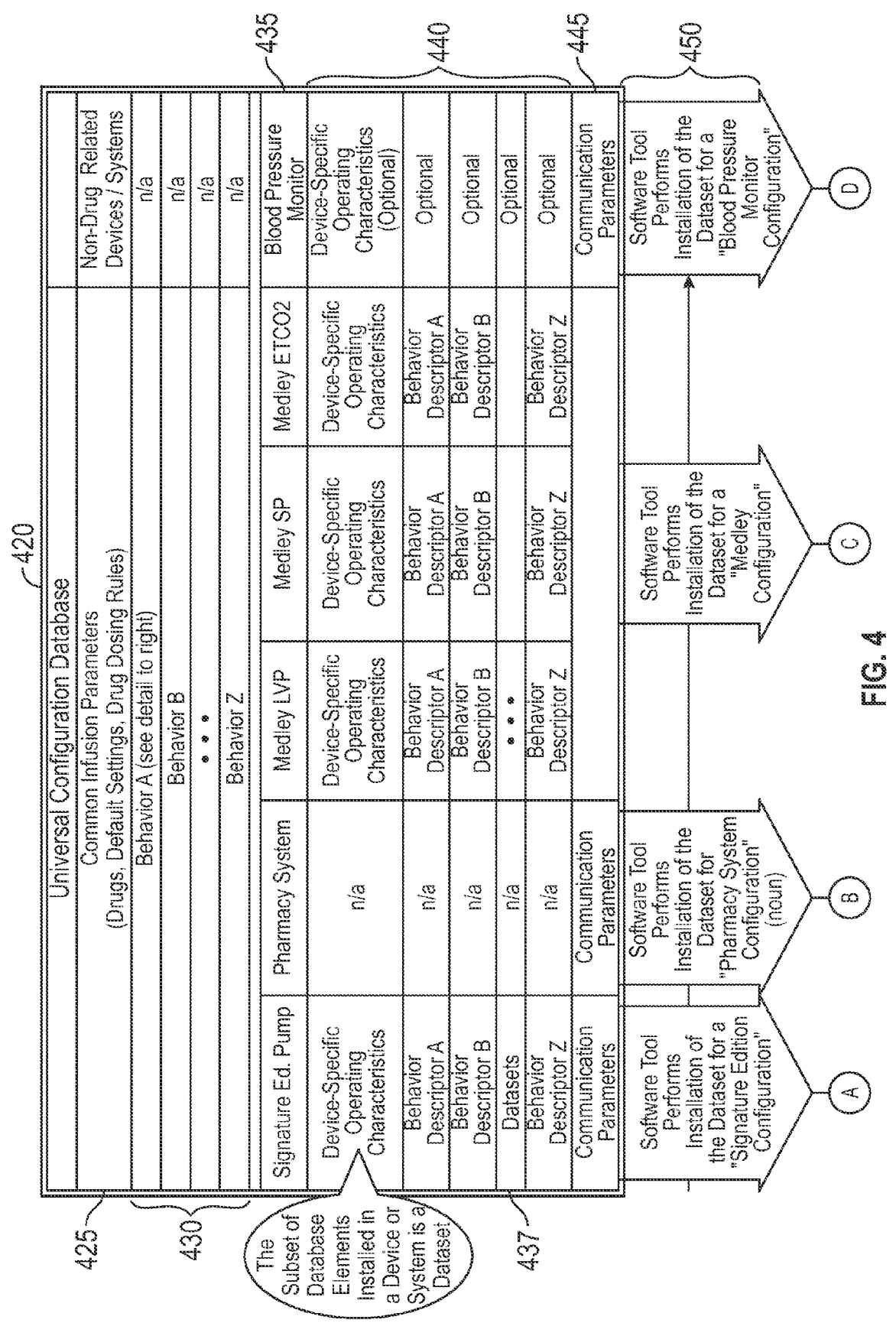
FIG. 4 is a schematic representation of various elements of one embodiment of the universal configuration database of FIG. 2.
Figure 4:
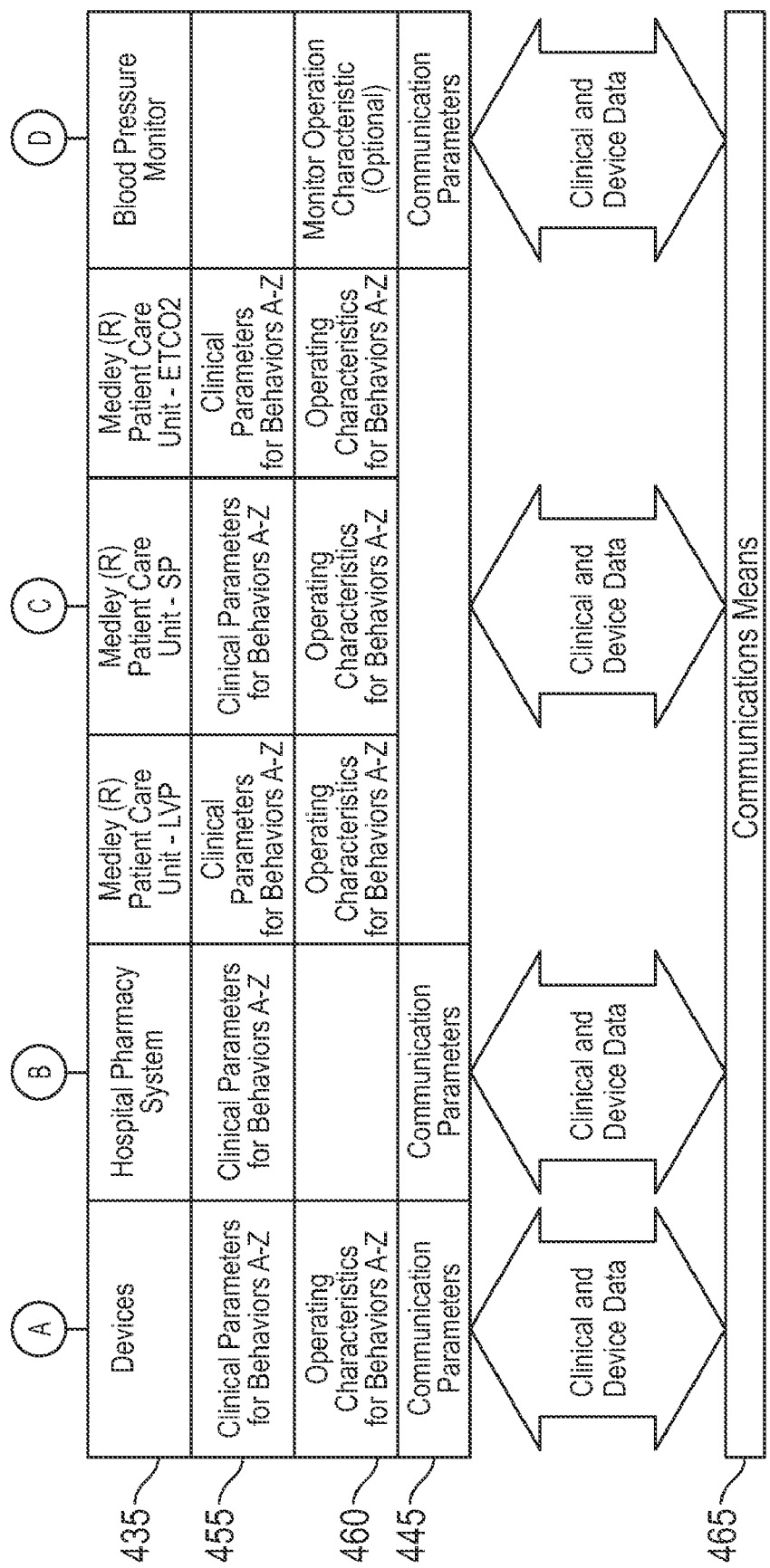

As discussed previously, the Device Type module 100 contains device-specific information for a plurality of patient care devices integrated into the configuration database 84 (FIG. 1). The device-specific information contained in each field of Device Types A, B and C, identified by reference numerals 102, 104, 106 respectively, generally includes device operating characteristics, such as device and functional module operating limits and/or various device features. As shown in FIG. 4, pump operating limits and available infusion features may be included where the patient care device is a type of infusion pump. Each Device Type 102, 104, 106 may also include a pointer 252 for identifying the records for that specific device.

Additional portions of the configuration database, such as the ensembles or rule sets described above, may also contain device-specific information and may be organized according to device type. In such cases, some or all of the ensembles may be contained within the Device Type module 100 or at least associated with the correct device type pointer 252 for identifying the relevant device types for that ensemble. In FIG. 3, the appropriate device-specific information from Device Type module 100 is shown loaded into the patient care device or system 48 and comprises pump limits and infusion features as discussed in more detail below.

As shown in FIGS. 2 and 3, the Pump Limits module 260 of configuration database 204 contains information that defines the overall operating limits of infusion pump module 52 and other pump devices, if any, attached to interface unit 50. The Pump Limits module 260 typically includes at least three fields, Air In Line (AIL) Limits 262, Max Rate 264, and Max Pressure 268. Because the Pump Limits module 260 of each configuration database 200, 202, 204, 206 potentially contains different parameters and values, module 260 helps define the operating characteristics or mode in which device 50 operates when a particular configuration database 200, 202, 204, 206 is active.

Air in Line (AIL) Limits 262 defines an allowable size of a single-bubble which may be passed through an infusion line connected to a patient and/or for the maximum percentage of air bubbles present which fall below the single-bubble threshold. Allowable AIL Limits may differ for particular patients or particular locations in the hospital. For example, an allowable limit of 50 μL may be set for pediatric patients, while a limit of 100-200 μL is used for general adult patients and 500 μL for operating room and/or trauma patients.

Max Rate 264 defines the maximum allowable infusion rate for an infusion pump operating under that particular configuration database 20. Again, the defined Max Rate 264 values may differ among patient class, attributes, location, and the like. For example, the maximum rate for delivering heparin to pediatric patients may be set at 10 units/Kg/hr, while adult patients have a limit of 500-1000 units/hr.

Feature Enable/Disable module 270 of configuration database 204 defines which particular features, such as infusion types for pumps, are available to the user of system 50 when configuration database 204 is activated for a particular device type. In a preferred embodiment of the present invention, patient care system 50 is capable of supporting a wide variety of such features, ranging from simple primary infusions used for hydration and keep-vein-open (KVO) applications to complex multichannel delivery applications. In one embodiment, the Feature Enable/Disable module 270 provides the device feature information for the various patient care device(s). In the embodiment in which there are multiple configuration databases, the Feature Enable/Disable module 270 further designates for each configuration database which of these features are enabled and disabled for that configuration.

Figure 5:
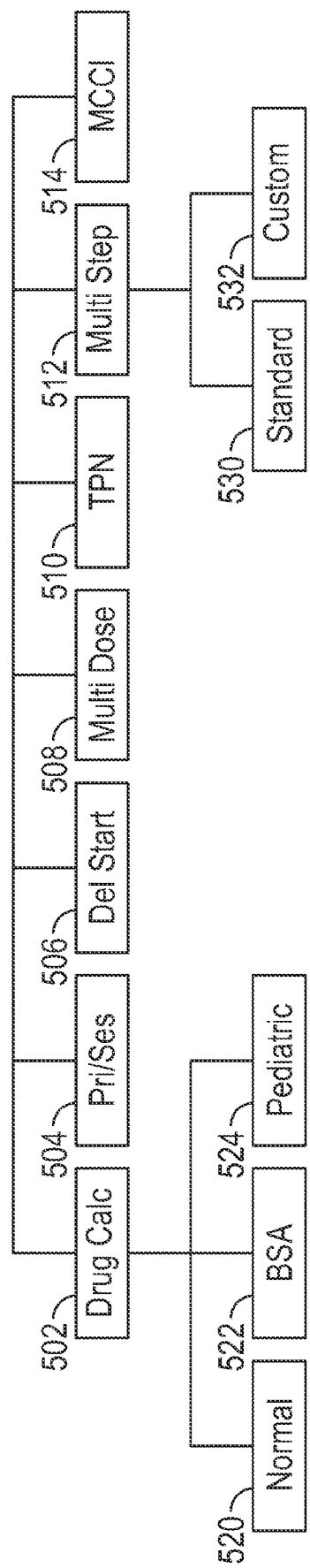
FIG. 5 is a block diagram illustrating a number of different infusion types supported by the interface unit of the present invention.

FIG. 5 illustrates some of the various features or infusion types that are supported by patient care system 50 according to one embodiment of the present invention. These features include, but are not limited to, Drug Calc 502, Primary/Secondary 504, Delayed Start (Del Start) 506, Multi Dose 508, Total Parenteral Nutrition (TPN) 510, Multi Step 512, and Multi-Channel Coordinated Intusion (MCCI) 514. As mentioned previously, each of these features or infusion types may be implemented by a particular ensemble of behavior characteristics that are defined by the information stored in the various fields and modules of a configuration dataset or behavior structure. The foregoing features are described briefly below; see U.S. Pat. No. 5,713,856, incorporated herein in its entirety, for a more detailed description of each.

Drug Calc 502 is a feature that allows calculation of drug infusion parameters such as rate or dose, based on patient weight, time units, and drug concentration. For example, the drug calculation function of the system allows the user to either: enter the desired drug dose and the infusion pump functional unit microprocessor calculates the correct flow rate to achieve the desired dose; enter the desired flow rate and the pump functional unit calculates the corresponding drug dose; or enter the desired bolus dose and the duration and the pump functional unit calculates the bolus rate and the VTBI. The system may additionally include a pediatric drug calculation function 524 which allows the user to enter, for example, flow rate, dose, and diluent volume. From these user entered parameters, the system calculates the amount of drug to admix with the diluent to achieve a drug concentration consistent with the selected dose and flow rate. Additional details regarding Drug Calc 502 features are found in U.S. Pat. No. 5,713,856.

Typically, Drug Calc 502 mode is used to ensure accuracy of infusion rate data where a user enters at least a portion of the infusion program data manually, e.g. through a touch screen or a keypad. For example, Drug Calc 502 may be used in conjunction with a drug-specific protocol such as stored in a configuration database. Alternatively, Drug Calc 502 feature may be used in combination with a stored ensemble that is identified by a coded label to calculate missing parameter values or to recalculate new values (for example, when a prescription includes a deviation from the standard protocol values).

Pri/Sec 504 feature allows use of ensembles utilizing a primary infusion in conjunction with a secondary infusion solution. Historically a primary infusion with an antibiotic secondary would be programmed by entering the primary and secondary rate and VTBI. In the present invention, a user can simply select the appropriate antibiotic regimen from the list infusion protocols and have the appropriate parameters automatically retrieved. The user may then simply confirm the parameters and start the infusion.

Delay Start 506 delays the start of an infusion protocol or other treatment for a particular duration of time or until a particular time of day. Alternatively, start may be delayed until the happening of a particular event. Such events include, but are not limited to, a signal from the interface unit in response to measured vital signs or other physiological parameters, completion of a stage of treatment by another module, or a signal or data received by system 50 over communication system 30.

Multi Dose 508 allows multiple doses of a drug to be delivered over time. An ensemble incorporating the Multi Dose 508 feature typically includes parameters for infusion rate, volume/dose, dose interval, number of doses and start time. As with all other ensembles stored in a configuration database, a stored Multi Dose 508 ensemble may be selected or activated from the configuration database simply by scanning a coded drug label containing the ensemble identifier (with or without instructions for deviating from default ensemble values). Any missing or different values may then be entered by the user.

TPN 510 provides for total parenteral nutrition delivery using standard or custom ramp and taper protocols known to those skilled in the art. For example, a typical TPN delivery protocol defined by a suitable ensemble of behavior characteristics defined by a configuration dataset for delivering 2500 calories over an eight hour period utilizes an initial slow rate of delivery with a gradual increase to a maintenance rate for a period of six to seven hours, then a gradual decrease to complete the infusion.

Multi Step 512 is similar to TPN 510 in that it allows delivery of a substance at various rates/volumes during a drug delivery or administration. Standard 530 defines standard multi-step drug delivery schedules that are commonly used without deviation for different patients. Custom 532 defines multi-step drug delivery schedules that are customized for particular situations. For example, a custom multi-step drug delivery schedule may be used for delivery of dobutamine to increase heart rate during a stress test. Such a protocol typically varies the delivery schedule of the drug to a patient over time, and patient weight or age is used as a factor to select a particular drug delivery schedule. Any number of custom multi-step delivery schedules may be defined and used by one skilled in the art.

MCCI 514 may be used in conjunction with Multi Dose 508 and/or Delay Start 506 features to program complex coordinated infusion involving different solutions being infused from multiple modules, or channels.

One skilled in the art will appreciate that the features and infusion types shown in FIG. 5 are intended to be illustrative of the present invention, and that patient care device 48 may support additional or different features than those described herein. Furthermore, the fields for other device types in the Device Type module 100 (FIG. 4) may include different categories and types of information than that described herein with respect to patient care device or system 48. In cases where there are multiple configuration databases supported for a particular device type, the device operating characteristics or other device-specific information for the device type may be the same or different among the various configurations.

Referring again to FIGS. 2-3, the Device Communications module 400 includes information to support communications between different types of patient care devices 402, 404, 406. The Device Communication module 400 may include fields for a Communication Protocol 408 and a Data Structure 410 for each type of patient care device 402, 404, 406 for which communication is to be supported. The Communication Protocol 408 and Data Structure 410 fields contain the information needed to establish communication with a particular type of patient care device. Any other fields necessary to define the "language" for a type of device may also be integrated in the Device Communications module 400.

With the Device Communication module 400 loaded into a device as shown in FIG. 2, the device has the means to make requests of another device accessible via a wired or wireless network, or other suitable communication means. For example, a device may send a query to a different device over the network, by providing an address and patient identification along with the desired query, and receive information from the queried device in response. Thus, different types of patient care devices such as infusion pumps, vital signs monitoring devices and physiological sensors that are not typically compatible with each other can now readily share information. The Device Communication Module is especially useful in conjunction with the Rule Sets module which often provides rules relating parameters of different patient care devices to each other.

Another aspect of an embodiment of the present invention is illustrated in FIG. 4. In this embodiment, an exemplary universal configuration database 420 consists of information that is structured to allow creation and modification of datasets 437 which are then used to configure and program various medical devices and systems with clinical and operating parameters so as to impart desired behaviors to the medical devices and systems.

As shown in FIG. 4, universal configuration database 420 includes common infusion parameters 425, such as, for example, a list of drugs, default settings and drug dosing rules, and parameters defining one or more clinical or operating behaviors 430. Universal configuration database 420 also includes device or system specific information, which may be organized as datasets 437. For example, the illustrated universal configuration database 420 includes datasets 437 for medical devices and systems 435, which are, for example, a Signature Edition® Gold pump, a Medley® LVP pump, a Medley® SP pump, a Medley® ETCO2 (end tidal $CO_2$) monitor, a blood pressure monitor and a pharmacy system. The Signature Edition Gold and Medley pumps, and the Medley ETCO2 monitor are products of ALARIS Medical Systems, Inc.

The datasets 437 of each of the above identified medical devices and systems include various clinical and operating parameters and rule sets that, in additional to any device specific characteristics, define one or more behavior descriptors 440 that program the medical device or system to act in a desired way. In other words, the medical devices and systems are programmed to behave in a way that is selected by the personnel of the institution.

Datasets 437 may also include appropriate communication parameters 445 to allow communication of the medical devices and systems with other devices, systems, and/or other institutional systems, as illustrated in FIG. 1, using appropriate communication means 465. The datasets 437 are typically installed using a software tool 450 into the appropriate medical device or system. The software installation tool imparts the desired behavior into the medical device or system by installing clinical parameters for various behaviors 455, operating characteristics for various behaviors 460 and suitable communication parameters 445 into medical devices and systems 435. The operation of such software installation tools is well known in the art and will not be described in detail herein.

Figure 6:
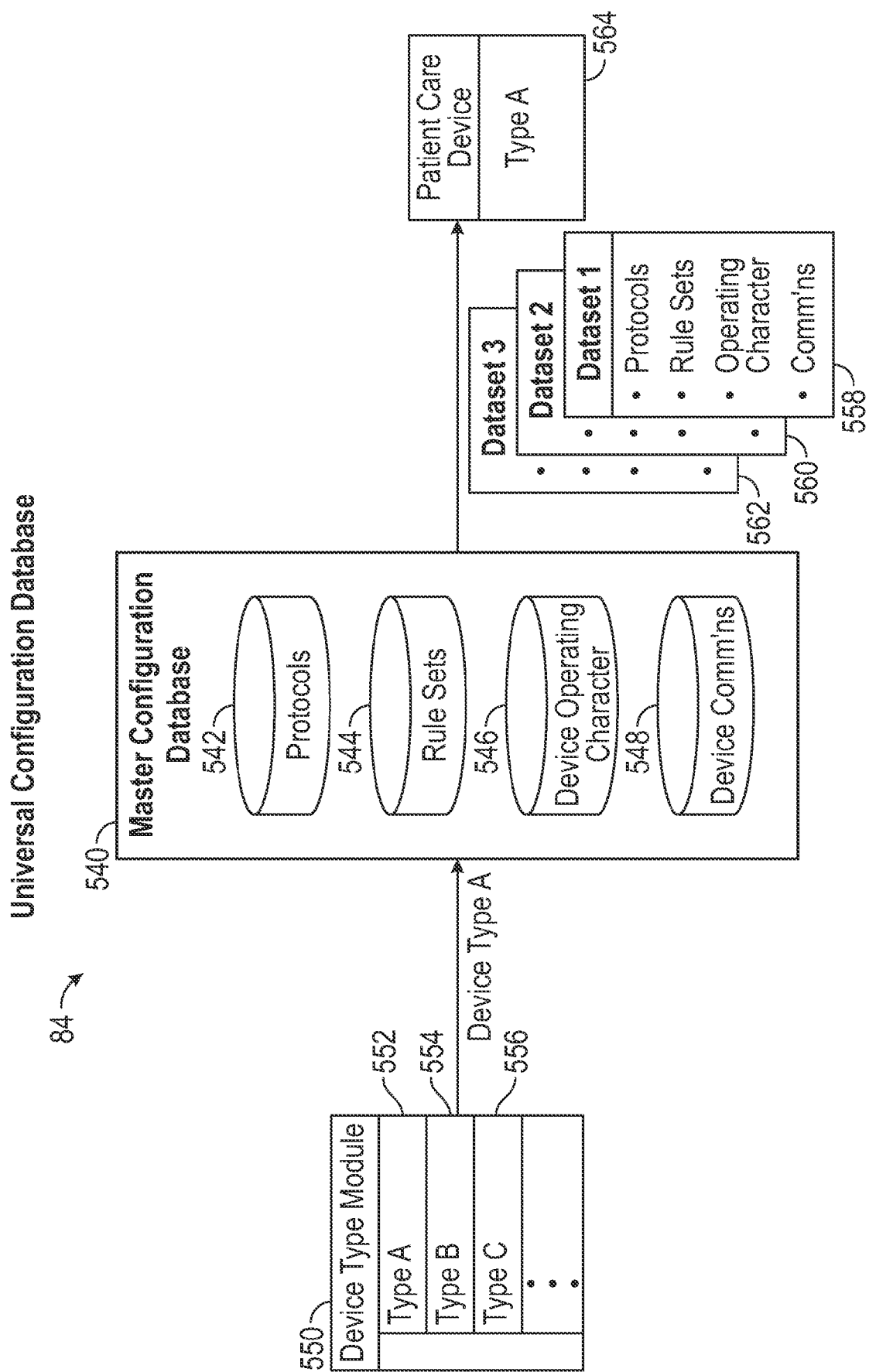
FIG. 6 is a schematic diagram illustrating another embodiment of a system for managing a universal configuration database including a common drug dosing rules library for patient care devices in accordance with aspects of the present invention.

Referring now to FIG. 6, an embodiment of the present invention is shown in which the universal configuration database 84 includes a master configuration database 540 that stores the various ensembles 542, rule sets 544, device operating characteristics 546 and device communication information 548 for each of the different device types. The ensembles 542, rule sets 544, device operating characteristics 546 and device communication information 548 may be stored as separate configuration databases, or otherwise organized into data sets, within the master configuration database 540. Each individual protocol, rule set, device operating characteristic and device communication information may be identified by a unique pointer for identifying and calling that data from the universal configuration database. The universal configuration database 84 further includes a separate Device Type Module 550 having fields for device types A, B and C, identified by reference numerals 552, 554 and 556, respectively, which contain reference links to the data in the master configuration database relevant to each particular device type. Thus, the data in the universal configuration database may be shared by the various device types and the editing module 86 (FIG. 1) may be used to enter and/or update data in the master configuration database 540 efficiently without duplicating entry of information used by multiple device types. In cases where the universal configuration database 84 also supports multiple configuration datasets, a device configuration module containing reference links to the master configuration database 540 may be used in conjunction with Device Type module 550 to further provide different configuration databases to the patient care devices.

Loading tool 88 (FIG. 2) selects a designated device type in the Device Type module 550, obtains the appropriate data from the master configuration database in accordance with the reference links, and builds a data set from that data in accordance with the designated device type. As shown in FIG. 6, upon selection of device type A, the relevant data for device type A is obtained from the master library 540 to create a data set, which may include one or more configuration databases. In the embodiment shown in FIG. 6, three different configuration datasets 1, 2, and 3, identified by reference numerals 558, 560 and 562, respectively, are created for device type A. The loading tool 58 then communicates the device-specific configuration datasets 558, 560 and 562 to a patient care device 564, which is, for example, a type A device and loads the datasets into the device to appropriately configure it. In one embodiment, patient care device 564 may be selected and identified by a user via user interface 52 (FIG. 1). Alternatively, the configuration management system 42 may be configured to recognize particular patient care devices in the network by querying the device and determining an identification of the device. In one embodiment, the identification of the device may comprise device type identification.

Figure 7:
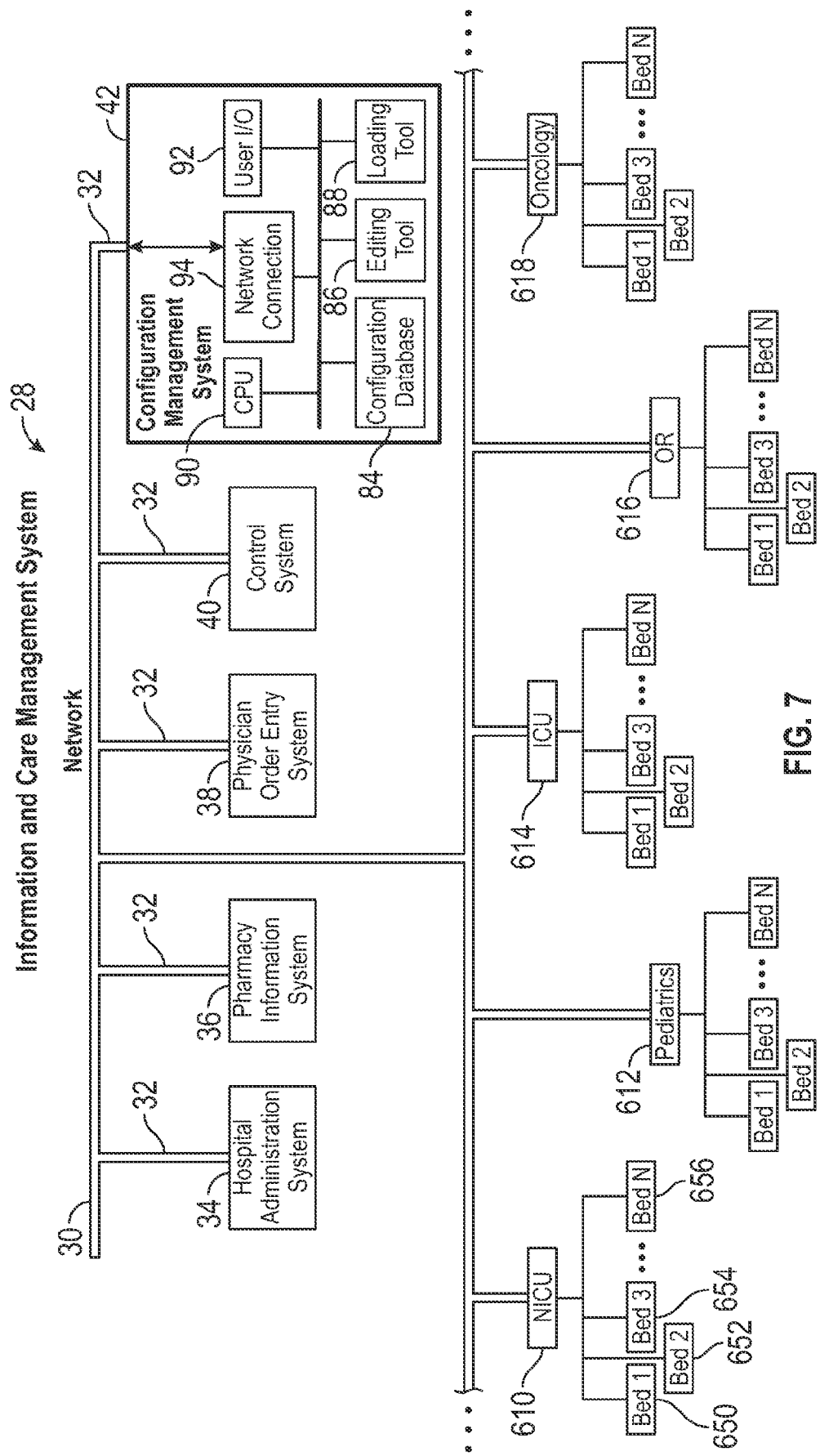
FIG. 7 is a schematic diagram of an alternative embodiment of the patient care management system of the present invention.

In one embodiment of the present invention, a plurality of patient care devices are linked through a local area network (LAN) to a floor or unit server as shown in FIG. 7. For example, in a neonatal intensive care unit (NICU) having an NICU server 610, a plurality of bedside patient care devices 650, 652, 654 and 656 are connected through a LAN 620 to unit server 610. Similar network servers may be provided throughout the hospital, such as pediatrics 612, intensive care unit (ICU) 614, surgery (OR) 616 and oncology 618. Unit server 610 may contain the configuration dataset information for the various types of patient care devices for that particular unit. The configuration datasets in patient care devices 650, 652, 654, 656 could be updated periodically by downloading them from the unit server. Alternatively, the appropriate device-specific configuration dataset could be downloaded from the server or system 42 as it is selected for use in patient care device 650, 652, 654 or 656. Still another alternative is to have a unit- or department-specific configuration dataset for the various types of devices that is automatically downloaded into a patient care device 650, 652, 654, 656 when the system is operatively connected to the department LAN. In any case, having some or all of the configuration dataset information stored in the unit server 610, 612, 614, 616, 618 facilitates management and updating of the databases. The configuration databases may also be stored in bedside CPUs which are situated in each private room, semi-private room, or ward area for monitoring or treating one or more patients. U.S. Pat. No. 5,718,442 to Engleson et al., which is incorporated herein by reference in its entirety, describes a system for connecting bedside medical devices to a hospital network, or network of networks, that may be suitable for use with the present invention.

In yet another embodiment, a universal configuration database containing datasets capable of configuring a device to operate in accordance with various behaviors depending on the use or location of the device may also be stored in the device. In this embodiment, for example, an infusion pump may have a dataset for configuring the pump for use in the ICU, in the pediatric ward, for delivery of oncology medications. The interface of the pump may allow a user to select a mode of operation from a menu of possible modes, which in actuality selects a dataset incorporating various ensembles of clinical and operating behaviors, or rule sets appropriate to the use for which the user is selecting the mode of operation.

Non-Networked Embodiment

In yet another alternative embodiment of the present invention, patient care devices and systems 44, 46, 48 (FIG. 1) are not directly connected to network 30. Rather, information is sent to the devices or systems indirectly over the network 30 using data input device 60, user interface 54, auxiliary interface 62 or other communication means. Such communication means include, but are not limited to, RS232 links, MIB systems, IR links, WLANS, portable data assistants, memory cards, portable storage media or any other suitable communication means. Indirect communication can also be accomplished, for example, using modems with either the traditional phone system, voice over data or with cellular phones. In one example, a portable computer such as a personal data assistant may be used to transfer the appropriate device-specific database information and/or infusion instructions from systems 36 and 42 to patient care devices and systems 44, 46, 48. The various possible means of direct and indirect communication allow information to be continuously or periodically transferred between the patient care device and other systems in network 30, such as, for example, hospital administration system 34, pharmacy information system 36, medical configuration management system 42, and the like.

Referring again to FIG. 1, regardless of how patient care devices 44, 46, 48 connect to or otherwise communicate with other systems in the healthcare facility, in one embodiment of the present invention, information is transferred, at least occasionally, between the various departments and systems within the facility such that functionality of patient care devices and systems 44, 46, 48 are altered by information received from the other systems. Such a distributed, coordinated care system provides for efficient utilization of assets and improved quality of patient care by maximizing integration and utility of information from various sources in the system and by limiting opportunities for human error. As discussed above, one example of how patient care device and system 44, 46 or 48 may alter its personality based upon information received from other sources is selection of a specific configuration dataset defining a particular, treatment location-specific (e.g. NICU, Pediatrics, ICU, Surgery, Oncology, etc.), operating behavior for the device. Similarly, prescription information, patient treatment history, drug incompatibilities, and the like from the pharmacy information system 32 are utilized to configure and control clinical devices and systems 44, 46, 48 and to minimize data entry errors.

By way of a non-limiting example, the use of the information and care management system 28 according to the present invention is explained in greater detail below by reference to procedures for configuring patient care devices and systems 44, 46, 48 for providing a prescribed treatment to a patient.

Most hospitals commonly have an established formulary of medications which defines how the medications are typically dispensed. When a patient care management system according to the present invention is first installed, a hospital committee may be formed to determine how that formulary would be applied to the patient care devices and systems 44, 46, 48. The configuration definitions (such as, for example, by hospital unit such as ICU, NICU, Pediatrics, Oncology, Surgery, etc.) are agreed upon and the drugs and typical infusion protocols and guidelines are established. In addition, all out-of-limit, or guard rail, conditions are defined. A biomedical engineer or other qualified personnel then enters the information into the universal configuration database management system via user interface 92 in order to customize the universal configuration database 84 for the particular institution. As discussed previously, with use of the editing tool 86, the user may edit entries that are common to different types of patient care devices at the same time. Device-specific entries, such as those for device operating characteristics, may be pre-entered by the manufacturer. Alternatively, the user may also enter these values into the universal configuration database 84. As the configuration datasets for different types of patient care devices have been integrated into one universal configuration database 84, the user can more efficiently and accurately provide standardized guidelines for use at the hospital. Alternatively, an institution may purchase, or otherwise be provided, with a universal configuration database, containing commonly used rule sets, ensembles, drug delivery schedules, out-of-limits events and the like, which may be used by the institution, or which may be modified by the institution as desired.

The entries for the Communication Protocol 408 and Data Structure 410 fields may either be entered into the library by the manufacturer and/or entered at the health care facility by qualified personnel, such as a biomedical engineer or other skilled technician, during customization of the universal configuration database. For example, the biomedical and information technology specialists at the health care facility typically have access to device characteristics, including communication protocols, for each device used at the facility. During customization of the universal configuration database, the specialist may enter the Communication Protocol 408 and Data Structure 410 data for the various types of devices used at the facility. For different devices marketed and/or licensed by a single manufacturer, the communication information for each device may be entered into the universal configuration database at the manufacturer level, thus eliminating the need for the technician to enter such information.

When all of the definitions are complete, then a configuration can be released for use in the institution's medical devices and systems. For example, infusion pumps at the institution may be configured, programmed or updated by transferring the device-specific configuration datasets into some or all of the institution's pumps. Transfer of the configuration dataset information typically occurs over communication system 30. Alternatively, configuration datasets may be downloaded/updated using removable media, portable computers, personal data assistants, or any other appropriate means for transferring information to patient care devices and systems 44, 46, 48.

The Loading Tool 88 causes the appropriate device-specific configuration datasets to be electronically loaded onto each of the target patient care devices at the hospital. The Loading Tool 88 automatically provides selective downloading of modules and information from the common library for each type of device as defined by the Device Type Module 100 or 550.

Assuring that the medication is being administered to the correct patient is also provided by this system. Upon entering the hospital every patient is typically issued an identification number (patient ID) and an associated wrist band. Printed on the band or located within the band is the patient ID in text form and in coded form. Various options exist for the coded ID. For example, the band could utilize a bar code, a magnetic strip, or any other means of storing coded patient identification information. The desired configuration database might also be recorded on the wrist band. For example, a child may have a band with an indicator that the pediatric configuration database is to be used.

The wrist band or ID device may also include a wireless device that allows the ID device or band to be governed by an appropriate device at the patient location to passively, if not automatically, identify the patient. The patient's identity would then be provided, using either wired or wireless communication means, to whatever equipment at the patient's location required it. Similar technology may be used in conjunction with medication labels, discussed in detail below.

Figure 8:
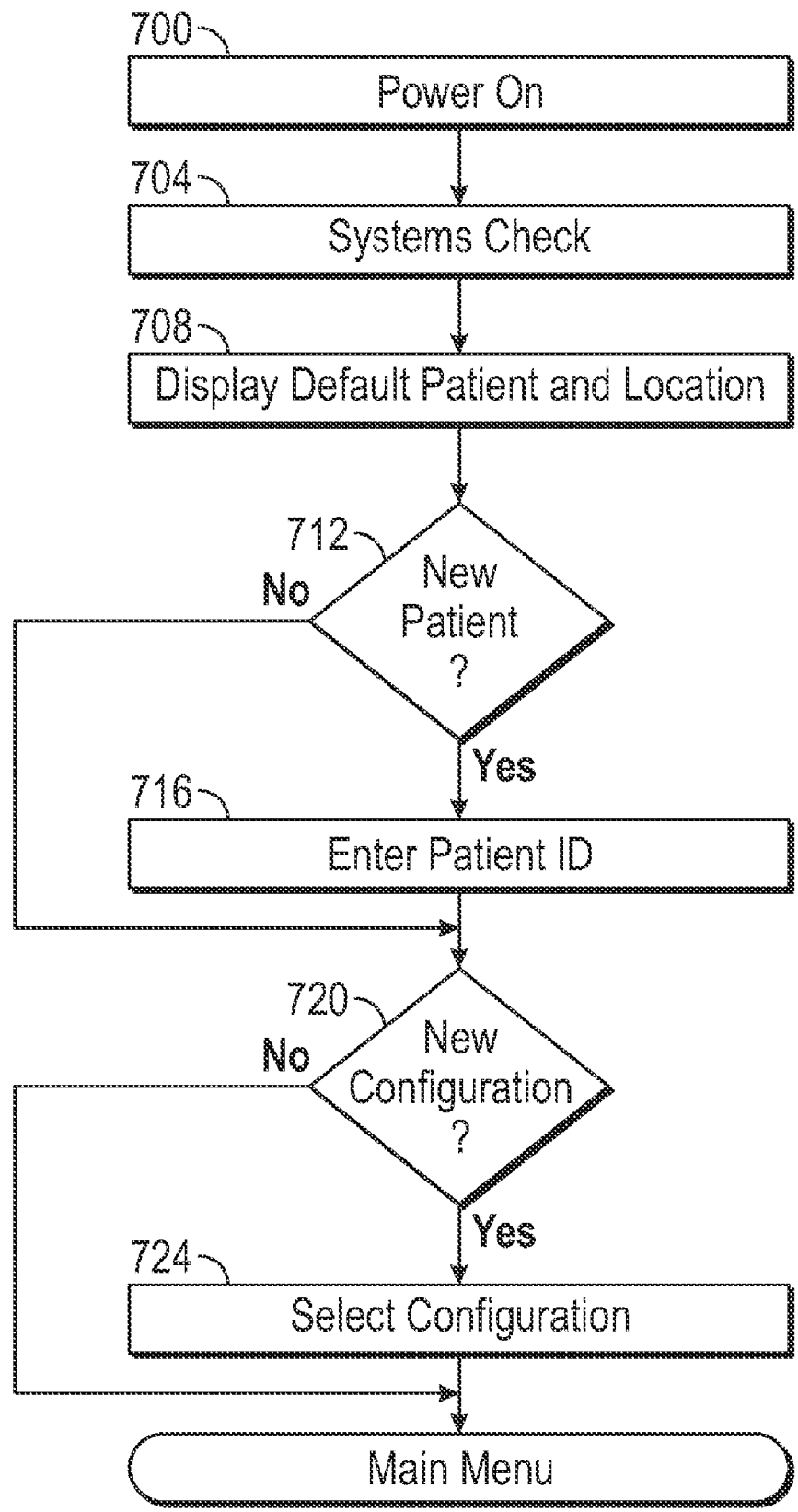
FIG. 8 illustrates the process steps used to relate a programming module with a patient, in accordance with one embodiment of the present invention.

The process steps involved in configuring a device to utilize a particular configuration dataset according to one embodiment of the present invention are shown in FIG. 8. After power to device or system 48 is turned on 700 and an internal systems check 704 is performed, the device displays on user interface 64 information pertaining to the current patient and/or the current location 708. In one embodiment of the invention, this information is recalled from the last use of the device. Alternatively, the device location and or patient identification may be determined by information received through the communication system 30 within the hospital. For example, referring to FIG. 7, a device 650 connected over LAN 620 to a server in NICU 610 receives information from the server that it should be located by Bed 1, and that a particular patient is scheduled to be in that bed. Accordingly, the device 650 utilizes that information as the default patient and location. Alternatively, device 650 automatically determines its location within the hospital by a sensor or other means of uniquely determining its location. A sensor is defined broadly herein as any device or process of sensing or detecting the location of a device, including, but not limited to, a network receptacle or port address, a network adapter, programmed location instructions, hospital records indicating location, an IR sensors or tags, RF sensors or tags, magnetic sensors or tags, or any other means of detecting the location of a device 650.

In step 712 the device queries the user whether the patient information is correct. If the patient is new to the device, or if the information is missing or incorrect, the user enters the patient ID in step 716. Patient ID is typically entered using input device 66, e.g., by scanning a patient's coded wristband including patient identification information. Alternatively, patient ID may be entered manually using a keyboard, keypad, or other interface device 64. If the current configuration dataset is missing or incorrect 720, the user is prompted to select the appropriate configuration dataset 724 such as, for example, by selecting a configuration dataset according to clinical location, patient, physician, and the like. Alternatively, the appropriate configuration dataset ID may scanned into the system from the patient's identification band, or may be automatically retrieved from memory or from another location in communication system 30 once the patient identity, location or other patient-specific information is entered into device or system 48.

When a physician orders an IV, the order is typically first sent to the pharmacy (where it is entered into the hospital's pharmacy information system 36). The order may either be written on a simple prescription slip or entered directly into the POE system 38 (FIG. 1). Most hospitals include a pharmacy computer system capable of maintaining records of medications already given as well as those prescribed in the future. Most commercially available pharmacy systems allow for adverse drug interactions to be checked for as part of the process prescription entering/drug dispensing process.

According to a preferred embodiment of the present invention, after the order is entered the prescription is prepared. If the drug is compounded or sourced in the pharmacy, then the prescribed medication is prepared and placed in a container. Pharmacy information system 36 would then translate the infusion order from the hospital pharmacy software onto a label with encoded message and accompanying text. The label preferably includes at least the following information: patient ID, infusion protocol reference, infusion protocol deviations, or deltas, if any, and scheduled time of infusion. The label is affixed to the medication container before the prescription is transported to the unit nursing station. Medications are preferably transported from the Pharmacy to the nurse's station by hospital personnel or contained within drug dispensing cabinets near the nurse's station. Alternatively, drugs may be transported using a robotic system, such as a PYXIS system (Pyxis Corporation, San Diego, Calif.). If the drug is to be distributed from a unit nursing station, then the same type of label may be printed at the station and affixed to the drug container.

At an appropriate time, the labeled medication container is then taken to the patient's location. The bar code reader (or other data input device, including passive devices designed to automatically query devices associated with the various ID and medication labels) is used to scan the coded drug label, the patient's coded ID band and the caregiver's ID badge, and optionally supplementary prescription information or medical device configuration instructions (including configuration dataset ID) printed on the label or an accompanying order, or otherwise made available for entry or downloading into the medical device or system once confirmation of the patient and medication is completed. The scanned information is stored in memory 62, while device or system 48 first compares the scanned data to ensure that the patient identity corresponds to the patient information on the medication label, and that the prescription is being administered at the appropriate time.

After the correct patient, prescription and time are verified, device or system 48 recalls from the active configuration database the protocol or other program information identified on the container label. The default parameter values are adjusted by any delta information included in the prescription. The user is prompted to enter, using a touch pad, bar code reader, or any other appropriate means, any missing or incomplete data. Optionally, some data may be obtained automatically via communication system 30 or from the appropriate department server based upon the entered patient ID, caregiver ID, user commands, etc. Once all required settings have been entered, central unit 50 displays the values, either serially or in one or more groups, to the user for verification. The configuration dataset is also accessed to check the entered infusion parameters according to the protocols, rule sets or other guidelines for that configuration. If any incorrect or out of range entries are detected, an alert may be activated to inform the operator. Once all information is entered and verified, interface unit 50 (FIG. 1) programs the functional module(s) 52, 54, 56 or 58 to perform the prescribed treatment.

It should be noted that the prescription label or other treatment instructions may identify multiple drug delivery schedules and other instructions. The multiple drug delivery schedules (or a single complex drug delivery schedule) may define a plurality of operations to be performed by device or system 48. For example, the prescription label or prescription order could identify a multichannel coordinated infusion drug delivery schedule involving multiple channels and infusion solutions. Additionally, the same order may identify a delivery schedule for (or detail instructions for) programming a functional module or auxiliary device to monitor the patient physiological parameters, such as a blood pressure, heart rate, $O_2$ saturation, respiratory rate, and the like. Interface unit 50 monitors the measured parameters and, depending upon active rule sets and other configuration instructions, can modify infusion parameters based upon signals received from the physiological monitors. Such feedback systems may be useful for titration of drugs, to control anesthesia, or to regulate blood pressure.

While several particular forms of the invention have been illustrated and described, it will be apparent that various modifications can be made without departing from the spirit and scope of the invention.

We claim:

1. A universal configuration database (UCDB) comprising:
   a protocol associated with a medication;
   an institutionally established guideline associated with one of a plurality of treatment locations, wherein the guideline comprises a maximum dose rate;
   a plurality of first data elements each comprising a device operating characteristic associated with one of the plurality of device types;
   a plurality of second data elements each comprising device communication information associated with one of the plurality of device types; and
   a device type module comprising a plurality of fields respectively associated with one of the plurality of device types, each field comprising at least one reference link to at least one of the data elements associated with the device type associated with the field; wherein:
   first and second datasets created from the UCDB respectively configure a first device type and a second device type to deliver the medication according to the protocol and the guideline,
   delivery of the medication by the first device type when loaded with the first dataset is equivalent to delivery of the medication by the second device type when loaded with the second dataset, and
   the second device type will not deliver the medication according to the protocol and the guideline when the second device type is loaded with the first dataset.

2. The UCDB of claim 1, wherein at least one of the data elements is identified by a unique pointer.

3. The UCDB of claim 1, wherein at least one of the data elements in the UCSB is shared by a plurality of device types.

4. The UCDB of claim 1, further comprising a plurality of third data elements each comprising a rule.

5. A patient care system that includes a plurality of patient care device types, the patient care system comprising:
   a universal configuration database (UCDB) comprising:
      a protocol associated with a medication;
      an institutionally established guideline associated with one of a plurality of treatment locations, wherein the guideline comprises a maximum dose rate;
      a plurality of device operating characteristics each associated with one of the plurality of device types;
      a plurality of device communication elements each associated with one of the plurality of device types; and
      a device type module comprising a plurality of fields respectively associated with one of the plurality of device types, each field comprising at least one reference link to at least one of the device operating characteristics and the device communication elements associated with the device type associated with the field; and
   a loading tool configured to:
      accept a designation of a first device type and a second device type, a medication, a protocol associated with the designated medication, and a treatment location;
      obtain the appropriate device operating characteristics and device communication elements from the UCDB in accordance with the reference links;
      build a first dataset and a second dataset that respectively configure the designated first device type and second device type to deliver the designated medication according to the designated protocol and implement the guideline associated with the designated treatment location from the obtained device operating characteristics and device communication elements;
      load the first dataset into a patient care device of the first device type; and
      load the second dataset into a patient care device of the second device type,
   wherein delivery of the medication by the first device type when loaded with the first dataset is equivalent to delivery of the medication by the second device type when loaded with the second dataset, and the second device type will not deliver the medication according to the protocol and the guideline when the second device type is loaded with the first dataset.

6. The patient care system of claim 5, wherein:
   more than one of the plurality of patient care device types are interchangeably usable to deliver a medication to a patient according to a protocol associated with the medication; and
   the plurality of patient care device types each operate according to device-specific operating characteristics.

7. The patient care system of claim 6, wherein:
   a first device type is related to a first type of infusion pump;
   a second device type is related to a second type of infusion pump that is different from the first type infusion pump;
   the first and second types of pumps can be used interchangeably to deliver the medication to a patient according to the protocol associated with the medication; and
   a dataset built for the first type of infusion pump cannot be used with the second type of infusion pump.

8. The patient care system of claim 5, wherein a dataset built by the loading tool for a first patient care device type cannot be loaded into any other patient care device type.

* * * * *